United States Patent [19]
Maurer et al.

[11] Patent Number: 5,663,189
[45] Date of Patent: Sep. 2, 1997

[54] 2-IMIDAZOLINYLAMINO HETEROCYCLIC COMPOUNDS USEFUL AS ALPHA-2 ADRENOCEPTOR AGONISTS

[75] Inventors: Peter Julian Maurer, Cincinnati; Jeffrey Joseph Ares, Fairfield; William Lee Seibel, Hamilton, all of Ohio; Daniel P. Walker, Bloomington, Ind.

[73] Assignee: The Procter & Gamble Company, Cincinnati, Ohio

[21] Appl. No.: 478,708

[22] Filed: Jun. 7, 1995

Related U.S. Application Data

[63] Continuation-in-part of Ser. No. 86,482, Jul. 1, 1993, abandoned.

[51] Int. Cl.$^6$ .................. A61K 31/415; C07D 405/12; C07D 409/12; C07D 233/50
[52] U.S. Cl. .................. 514/397; 548/311.4; 548/311.7
[58] Field of Search .................. 548/311.4, 311.7; 514/397

[56] References Cited

U.S. PATENT DOCUMENTS

| | | | |
|---|---|---|---|
| 4,588,736 | 5/1986 | Esser et al. | 514/392 |
| 4,980,364 | 12/1990 | Goodman | 514/377 |
| 5,091,528 | 2/1992 | Gluchowski et al. | 544/105 |

FOREIGN PATENT DOCUMENTS

| | | |
|---|---|---|
| 3326274 | 1/1985 | Germany . |
| 54-12374 | 1/1979 | Japan . |
| 62-99375 | 5/1987 | Japan . |
| 1016514 | 1/1966 | United Kingdom . |

OTHER PUBLICATIONS

Chapleo, C.B., J. C. Doxey, L. W. Frank, P.L. Myers, A.G. Roach, C.F.C. Smith & N.K. Virdee, "Comparison of the α–Adrenoceptor Profiles of Clonidine and Two Oxygenated Arylamino Imidazolines", *European Journal of Pharmacology*, vol. 91 (1983), pp. 123–128.

Chapleo, C.B., J.C. Doxey, P.L. Myers, M. Myers, C.F.C. Smith & M.R. Stillings, "Effect of 1,4–Dioxanyl Substitution on the Adrenergic Activity of Some Standard α–Adrenoreceptor Agents", *European Journal of Medical Chemistry*, vol. 24 (1989), pp. 619–622.

Chapleo, C.B., R.C.M. Butler, D.C. England, P.L. Myers, A.G. Roach, C.F.C. Smith, M.R. Stillings & I.F. Tulloch, "Heteroaromatic Analogues of the α$_2$–Adrenoreceptor Partial Agonist Clonidine", *Journal of Medical Chemistry*, vol. 32 (1989), pp. 1627–1630.

Clare, K.A., M.C. Scrutton & N.T. Thompson, "Effects of α$_2$–Adrenoreceptor Agonists and of Related Compounds on Agregation of, and on Adenylate Cyclase Activity in, Human Platelets", *British Journal of Pharmacology*, vol. 82 (1984), pp. 467–476.

*Primary Examiner*—Patricia L. Morris
*Attorney, Agent, or Firm*—Milton B. Graff; Mary Pat McMahon; Richard A. Hake

[57] ABSTRACT

The subject invention relates to compounds having the structure:

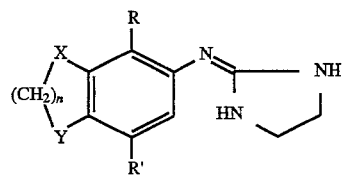

wherein (a) n is an integer from 1 to about 3;

(b) X and Y are each independently selected from O, S and $CH_2$, with at least one of X and Y being O or S;

(c) R is unsubstituted, straight or branched chain alkanyl or alkanoxy having from 1 to about 3 non-hydrogen atoms; and (d) R' is selected from hydrogen, methyl, cyano, and halo; pharmaceutical compositions containing such compounds; and the use of such compounds for preventing or treating one or more of respiratory disorders, ocular disorders, and gastrointestinal disorders.

22 Claims, No Drawings

2-IMIDAZOLINYLAMINO HETEROCYCLIC COMPOUNDS USEFUL AS ALPHA-2 ADRENOCEPTOR AGONISTS

This is a continuation-in-part of application Ser. No. 08/086,482, filed on Jul. 1, 1993, now abandoned.

TECHNICAL FIELD

The subject invention relates to certain substituted 2-imidazolinylamino heterocyclic compounds. The compounds have been found to be selective alpha-2 adrenoceptor agonists and are useful for treatment of one or more respiratory disorders, particularly nasal congestion; ocular disorders, particularly glaucoma; and gastrointestinal disorders, particularly diarrhea.

BACKGROUND OF THE INVENTION

Compounds related in structure to those of the subject invention are disclosed in the following references: Chapleo, C. B., J. C. Doxey, L. W. Frank, P. L. Myers, A. G. Roach, C.F.C. Smith & N. K. Virdee, "Comparison of the α-Adrenoceptor Profiles of Clonidine and Two Oxygenated Arylamino Imidazolines", *European Journal of Pharmacology*, Vol. 91 (1983), pp. 123–128; Chapleo, C. B., J. C. Doxey, P. L. Myers, M. Myers, C.F.C. Smith & M. R. Stillings, "Effect of 1,4-Dioxanyl Substitution on the Adrenergic Activity of Some Standard α-Adrenoreceptor Agents", *European Journal of Medicinal Chemistry*, Vol. 24 (1989), pp. 619–622; Chapleo, C. B., R.C.M. Butler, D. C. England, P. L. Myers, A. G. Roach, C.F.C. Smith, M. R. Stillings & I. F. Tulloch, "Heteroaromatic Analogues of the α$_2$-Adrenoreceptor Partial Agonist Clonidine", *J. Med. Chem.*, Vol. 32 (1989), pp. 1627–1630; Clare, K. A., M. C. Scrutton & N. T. Thompson, "Effects of α$_2$-Adrenoceptor Agonists and of Related Compounds on Aggregation of, and on Adenylate Cyclase Activity in, Human Platelets", *Br. J. Pharmac.*, Vol. 82 (1984), pp. 467–476; British Patent Specification No. 1,016,514 of Boehringer Ingelheim G.m.b.H., published Jan. 12, 1966; Japanese Patent Application No. 62-99375 of Kowa K. K., published May 8, 1987; Japanese Patent Application No. 54-12374 of Kowa Co., Ltd., published Jan. 30, 1979; German Patent Application No. 3,326,274 of Boehringer Ingelheim KG, published Jan. 31, 1985; and U.S. Pat. No. 5,091,528 issued to Gluchowski on Feb. 25, 1992. However, many compounds related in structure to those of the subject invention provide neither the activity nor the specificity desirable when treating respiratory, ocular or gastrointestinal disorders.

It is particularly relevant to the subject invention that compounds found to be effective nasal decongestants are frequently found to have undesirable side effects, such as causing hypertension and insomnia. There is a need for new drugs which provide relief from nasal congestion without causing these undesirable side effects.

It is an object of the subject invention to provide novel compounds having substantial activity in preventing or treating nasal congestion.

It is a further object of the subject invention to provide such compounds which do not cause hypotension, drowsiness, hypertension, insomnia or other undesirable side effects.

It is also an object of the subject invention to provide novel compounds for treating cough, chronic obstructive pulmonary disease (COPD) and/or asthma.

It is also an object of the subject invention to provide novel compounds for treating glaucoma and/or diarrhea.

It is a still further object of the subject invention to provide such compounds which have good activity from peroral and/or topical dosing.

SUMMARY OF THE INVENTION

The subject invention relates to compounds having the structure:

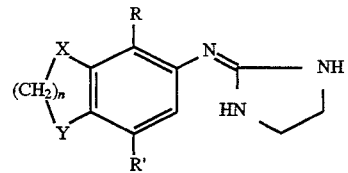

wherein
(a) n is from 1 to about 3;
(b) X and Y are each independently selected from O, S and CH$_2$, with at least one of X and Y being O or S;
(c) R is unsubstituted, straight or branched chain alkanyl or alkanoxy having from 1 to about 3 non-hydrogen atoms; and
(d) R' is selected from hydrogen, methyl, cyano, and halo; pharmaceutical compositions containing such compounds; and the use of such compounds for preventing or treating respiratory, ocular, and/or gastrointestinal disorders.

DETAILED DESCRIPTION OF THE INVENTION

As used herein, "alkanyl" means a saturated hydrocarbon chain. Unless otherwise specified, preferred alkanyl is unsubstituted; also, preferred alkanyl is straight chain.

As used herein, "alkanoxy" means O-alkanyl.

As used herein, "halo" means fluorine, chlorine, bromine, and iodine. Unless otherwise specified, preferred halo are fluorine, chlorine and bromine; more preferred are fluorine and chlorine; most preferred is fluorine.

The subject invention involves novel compounds having the following structure:

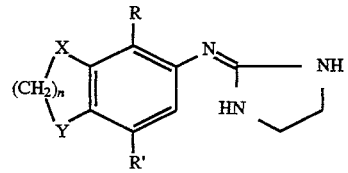

In the above structure, n is from 1 to about 3, preferably 1 or 2.

In the above structure, X and Y are each independently selected from O, S, and CH$_2$, with at least one of X and Y being O or S. Preferred is X and Y both being O or S; more preferred is both X and Y being O. Also preferred is X being O or S and Y being CH$_2$; more preferred is X being O and Y being CH$_2$. Also preferred is Y being O and X being CH$_2$.

In the above structure, R is unsubstituted, straight or branched chain alkanyl or alkanoxy having from 1 to about 3 atoms other than hydrogen. Preferred R is alkanyl. Preferred alkanyl R is methyl or ethyl, especially methyl. Preferred alkanoxy R is methoxy or ethoxy.

In the above structure R' is selected from hydrogen, methyl, cyano, and halo. Preferred R' is methyl or hydrogen, especially hydrogen.

In the above structure when X is O or S, preferably O, preferred R is methyl or ethyl and R' is cyano or hydrogen.

Also preferred is R being ethyl and R' being methyl or halo. Also preferred is R being methoxy and R' being methyl or halo.

When X is $CH_2$ and Y is O, preferred is R being methyl or ethyl and R' being hydrogen, methyl or halo, especially methyl. When Y is $CH_2$, and X is O or S, preferred is R' being H.

Preferred compounds of the subject invention include those having the above structure with the moieties indicated in the following table:

| Compound No. | n | X | Y | R | R' |
|---|---|---|---|---|---|
| 1 | 2 | O | O | Me | H |
| 2 | 1 | O | O | Me | H |
| 3 | 2 | O | O | Me | Me |
| 4 | 1 | O | O | Me | Me |
| 5 | 2 | $CH_2$ | O | Me | Me |
| 6 | 1 | O | $CH_2$ | Me | H |

The compounds of the subject invention are particularly useful for the treatment of respiratory disorders, especially nasal congestion associated with allergies and colds. Treatment can also be useful for other nasal disorders as well as their sequellae (for example, sinusitis and otitis). At the same time, it has been found that undesired side effects, such as hypotension, drowsiness, hypertension, or insomnia can be avoided. While not limited to a particular mechanism of action, the subject compounds are believed to provide advantages in the treatment of nasal decongestion over related compounds through their ability to interact with alpha-2 adrenoceptors. The subject compounds have been found to be alpha-2 adrenoceptor agonists which cause constriction of peripheral vascular beds in the turbinates, and have little or no effect on the central nervous system.

The compounds of the subject invention are also useful for the treatment of ocular disorders associated with increased intraocular pressure, such as glaucoma. The compounds are administered either perorally, or topically as drops, gels or creams directly to the surface of the mammalian eye.

The compounds of the subject invention are also useful for controlling gastrointestinal motility disorders, such as diarrhea, by antimotility and antisecretory actions on the gastrointestinal tract.

The pharmacological activity and selectivity of the subject compounds can be determined using published test procedures. The alpha-2 selectivity of the compounds is determined by measuring receptor binding affinities and in vitro functional potencies in a variety of tissues known to possess alpha-2 and/or alpha-1 receptors. (See, e.g., *The Alpha-2 Adrenergic Receptors*, L. E. Limbird, ed., Humana Press, Clifton, N.J.) The following in vivo assays are typically conducted in rodents or other species. Central nervous system activity is determined by measuring locomotor activity as an index of sedation. (See, e.g., Spyraki, C. & H. Fibiger, "Clonidine-induced Sedation in Rats: Evidence for Mediation by Postsynaptic Alpha-2 Adrenoreceptors", *J. Neural. Trans.*, Vol. 54 (1982), pp. 153–163). Nasal decongestant activity is measured using rhinomanometry as an estimate of nasal airway resistance. (See, e.g., Salem, S. & E. Clemente, "A New Experimental Method for Evaluating Drugs in the Nasal Cavity", *Arch. Otolarynng*, Vol. 96 (t972), pp. 524–529). Antiglaucoma activity is determined by measuring intraocular pressure. (See, e.g., Potter, D., "Adrenergic Pharmacology of Aqueous Human Dynamics", *Pharmacol. Rev.*, Vol. 13 (1981), pp. 133–153). Antidiarrheal activity is determined by measuring the ability of the compounds to inhibit prostaglandin-induced diarrhea. (See, e.g., Thollander, M., P. Hellstrom & T. Svensson, "Suppression of Castor Oil-Induced Diarrhea by Alpha-2 Adrenoceptor Agonists", *Aliment. Pharmacol. Therap.*, Vol. 5 (1991), pp. 255–262). Antiasthma activity is determined by measuring the effect of the compound on bronchoconstriction associated with pulmonary challenges such as inhaled antigens. (See, e.g., Chang, J. J. Musser & J. Hind, "Effects of a Novel Leukotriene $D_4$ Antagonist with 5-Lipoxygenase and Cyclooxygenase Inhibitory Activity, Wy-45,911, on Leukotriene-$D_4$- and Antigen-Induced Bronchoconstriction in Guinea Pig", *Int. Arch. Allergy Appl. Immun*, Vol. 86 (1988), pp. 48–54; and Delehunt, J., A. Perruchound, L. Yerger, B. Marchette, J. Stevenson & W. Abraham, "The Role of Slow-Reacting Substance of Anaphylaxis in the Late Bronchial Response After Antigen Challenge in Allergic Sheep", *Am. Rev. Respir. Dis.*, Vol. 130 (1984), pp. 748–754). Activity in cough is determined by measuring the number and latency of the cough response to respiratory challenges such as inhaled citric acid. (See, e.g., Callaway, J. & R. King, "Effects of Inhaled Alpha-2-Adrenoceptor and $GABA_B$ Receptor Agonists on Citric Acid-Induced Cough and Tidal Volume Changes in Guinea Pigs", *Eur. J. Pharmacol.*, Vol. 220 (1992), pp. 187–195).

The compounds of the subject invention are synthesized using the following general procedures:

Scheme I

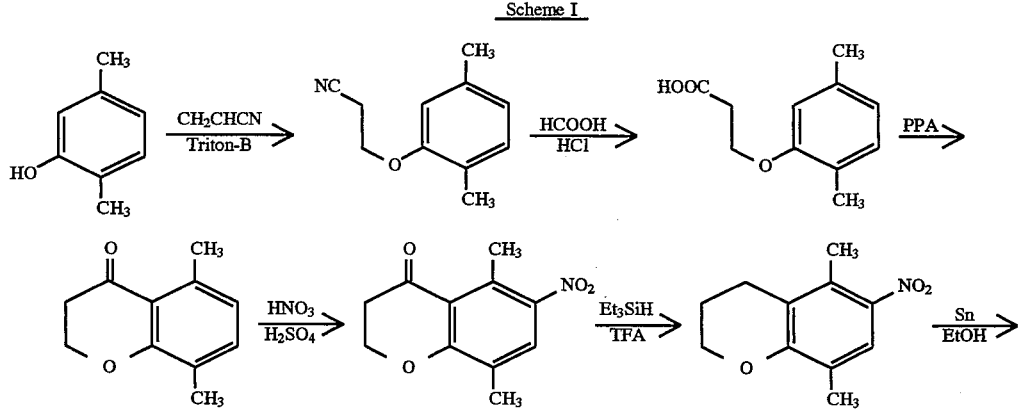

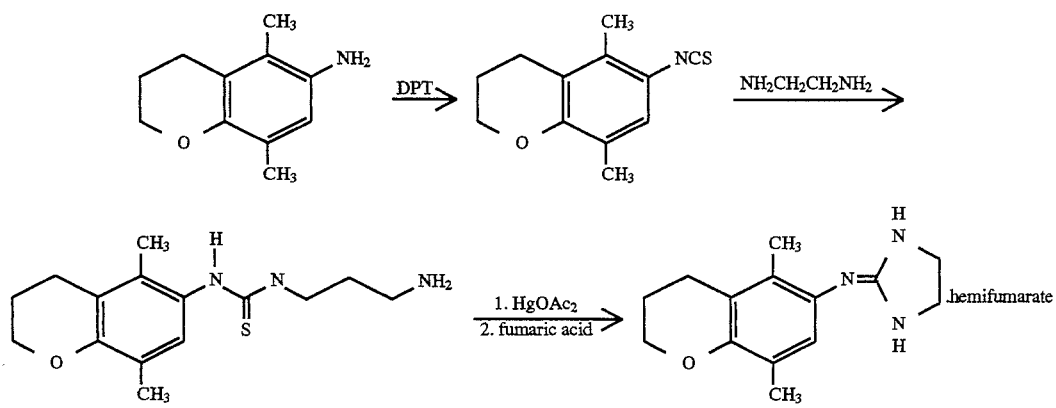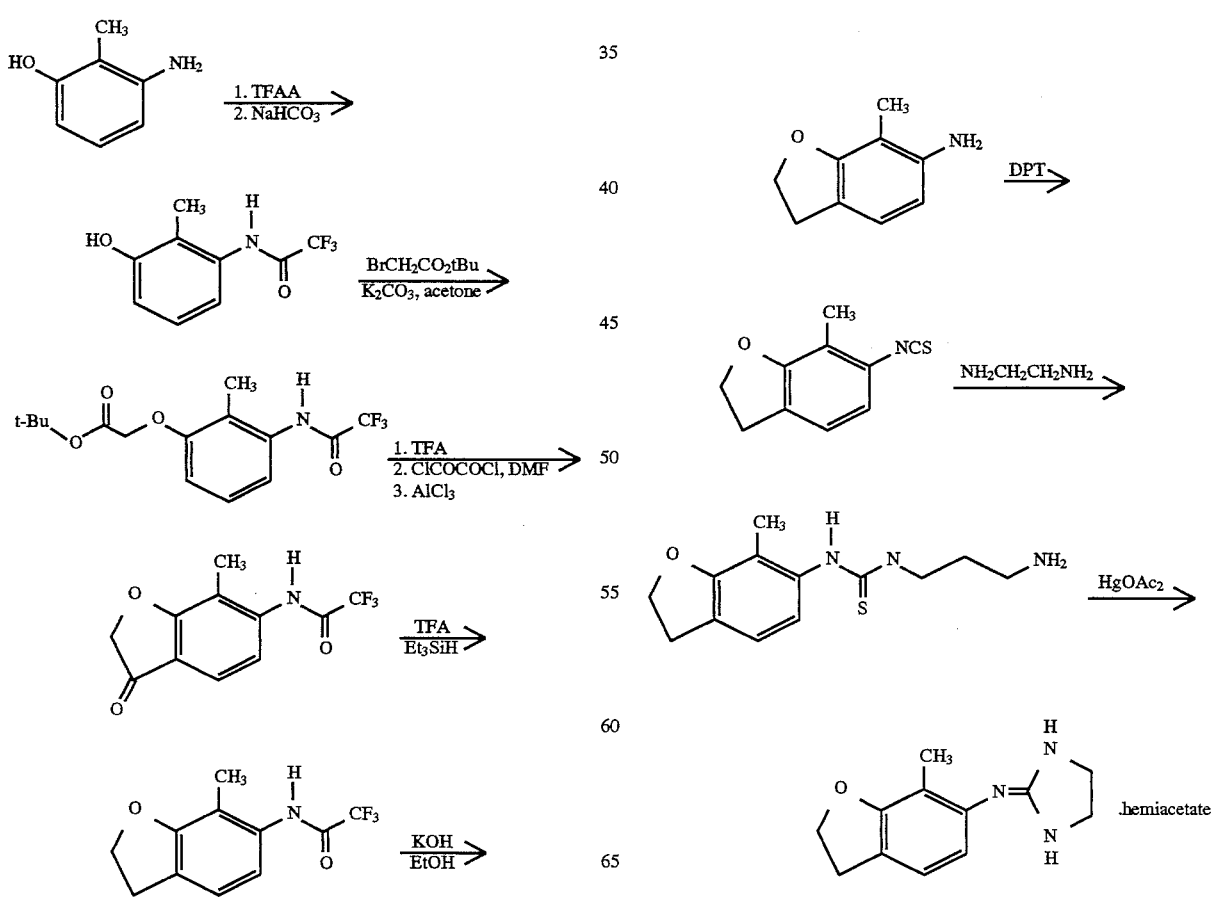

Scheme III

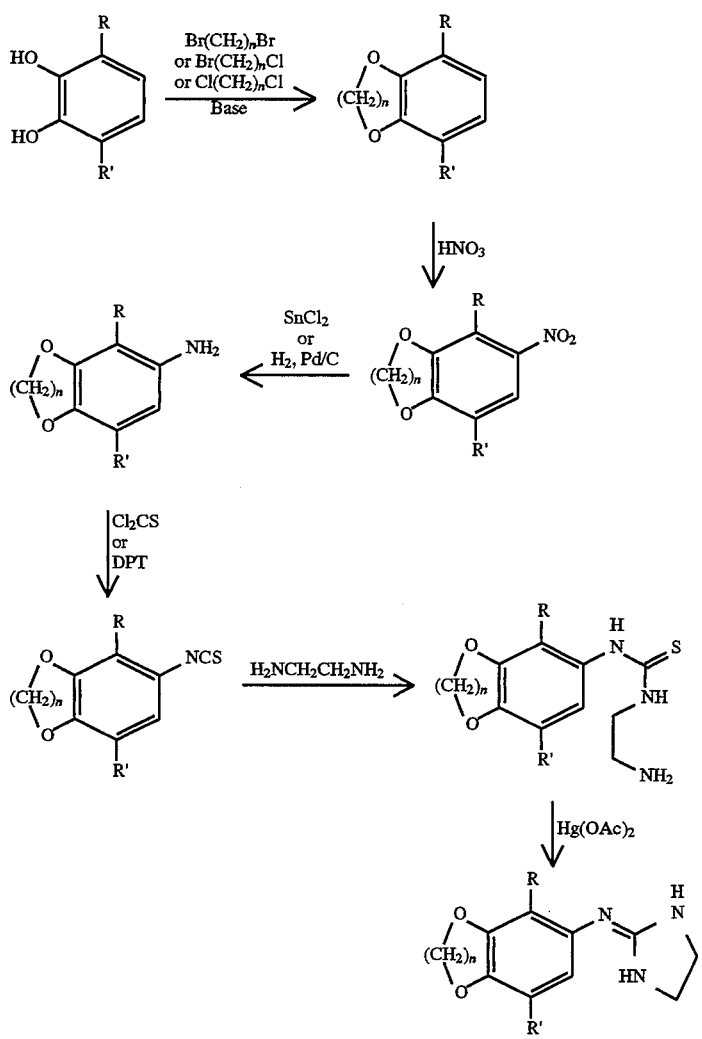

The following non-limiting examples provide details for the syntheses of compounds of the subject invention.

Example 1

5-Methylbenzodioxan. 63.1 g of potassium tert-butoxide, 34.9 g of 3-methylcatechol and 29 mL of 1,2-dibromoethane in 200 mL of DMSO are heated to 70° C. and stirred under argon. Three more 10 mL portions of 1,2-dibromoethane am added after 3, 4 and 5 hours. After a total of 16 hours, the mixture is cooled, poured into 1200 mL of water, and extracted with ether. The extracts are washed three times with 1N NaOH and once with water, then dried over sodium sulfate and concentrated. The residue is distilled under oil pump vacuum, and the portion distilling from 60° to 65° C. is collected and found to be 12.5 g of 5-methylbenzodioxan.

5-Methyl-6-nitrobenzodioxan and 5-methyl-7-nitrobenzodioxan. 11.9 g of 5-methylbenzodioxan is dissolved in 100 mL of acetic anhydride and cooled to 0° C., excluding moisture. 5.55 mL of concentrated nitric acid (specific gravity=1.41) is added dropwise over 30 minutes with stirring. After an additional 30 minutes at 0° C., the mixture is poured onto crushed ice. The resulting solid is collected by filtration and found to be 14.8 g of a mixture of 5-methyl-6-nitrobenzodioxan and 5-methyl-7-nitrobenzodioxan.

6-Amino-5-methylbenzodioxan. The above mixture is dissolved in 300 mL of ethanol and treated with 72 g of tin(II) chloride. The mixture is refluxed for 18 hours under argon. The mixture is cooled and poured into 2 L of saturated aqueous sodium bicarbonate. Enough 50% sodium hydroxide solution is added to dissolve the precipitated tin salts, and the mixture is extracted with chloroform. The extracts are dried over potassium carbonate and concentrated. The residue is found to be 11.5 g of a mixture of 6-amino-5-methylbenzodioxan and 7-amino-5-methylbenzodioxan. The isomers are separated by chromatography on silica gel, eluting with a 60:40 mixture of chloroform and hexanes. The 6-aminoisomer elutes ahead of the 7-aminoisomer.

6-Isothiocyanato-5-methylbenzodioxan. 1.90 g of 6-amino-5-methyl-benzodioxan is dissolved in 50 mL of water containing 11.8 mL of 1.0N hydrochloric acid. 1.10 mL of thiophosgene is added dropwise while stirring vigorously. After 4 hours of stirring at room temperature, the mixture is made basic with 50% sodium hydroxide solution, and then extracted with methylene chloride. The extracts are dried over sodium sulfate and concentrated. The residue is found to be 2.0 g of 6-isothiocyanato-5-methylbenzodioxan.

6-[N'-(2-aminoethyl)-1-thiouriedo]-5-methylbenzodioxan. A solution of 2.0 g of 6-isothiocyanato- 5-methylbenzodioxan dissolved in 20 mL of methylene chloride is added dropwise to a solution of 3.23 mL of ethylenediamine in 50 mL of methylene chloride while stirring at room temperature. After 45 minutes of further stirring, the solvent is evaporated under vacuum and excess ethylenediamine is evaporated under vacuum at 50° C. The crude residue is found to contain 2.83 g of 6-[N'-(2-aminoethyl)-1-thiouriedo]-5-methylbenzodioxan.

6-(2-Imidazolinylamino)-5-methylbenzodioxan. A solution of the above 6-[N'-(2-aminoethyl)-1-thiouriedo]-5-methylbenzodioxan in 50 mL of methanol is treated with 3.37 g of mercury(II) acetate. After stirring at room temperature for 14 hours, the mixture is filtered, and the solvent is evaporated under vacuum. The residue is partitioned between saturated aqueous sodium bicarbonate and methylene chloride. The aqueous layer is separated, made strongly basic with 50% aqueous sodium hydroxide and extracted with methylene chloride. The extracts are dried over potassium carbonate and concentrated under vacuum. The residue is found to be 1.77 g of 6-(2-imidazolinylamino)-5-methylbenzodioxan.

6-(2-Imidazolinylamino)-5-methylbenzodioxan fumarate salt. 1.73 g of 6-(2-imidazolinylamino)-5-methylbenzodioxan and 0.861 g of fumaric acid are dissolved in 20 mL of methanol. The solution is heated and treated with about 20 mL of ether. After cooling, the crystals which formed are collected and found to be 2.14 g of 6-(2-imidazolinylamino)-5-methylbenzodioxan fumarate salt, which melts at 199°–201° C.

Example 2

4-Methyl-1,3-benzodioxole. To a stirred solution of 11.00 g of 3-methylcatechol and 7.09 g of sodium hydroxide in 10 mL of dry dimethylsulfoxide is added 6.34 mL of dichloromethane. A reflux condenser is attached and the mixture heated in an oil bath to 120° C. for 30 minutes. The mixture is allowed to cool to room temperature and then is distributed between 50 mL of water and 200 mL of chloroform. The chloroform layer is dried over magnesium sulfate and concentrated under reduced pressure to yield a red liquid, which is purified by chromatography on silica gel to afford 3.0 g of 4-methyl-1,3-benzodioxole as a light yellow liquid.

5-Nitro-4-methyl-1,3-benzodioxole and 6-Nitro-4-methyl-1,3-benzodioxole. A solution of 1.42 mL of concentrated nitric acid in 20 mL of acetic anhydride is added dropwise to a stirred solution of 2.90 g of 4-methyl-1,3-benzodioxole in 75 mL of acetic anhydride at −5° C. After 15 minutes the mixture is poured over 100 g of crushed ice and allowed to stir for 30 minutes as a yellow precipitate falls out of solution. The solid is filtered and taken up in chloroform, dried over magnesium sulfate and concentrated under reduced pressure to afford 2.85 g of an inseparable mixture of 5-nitro-4-methyl-1,3-benzodioxole and 6-nitro-4-methyl-1,3-benzodioxole.

5-Amino-4-methyl-1,3-benzodioxole. 2.85 g of the above mixture is mixed with 0.30 g of 5% palladium on carbon in 75 mL of methanol and placed under a 50 psi hydrogen atmosphere. The mixture is shaken for three hours at room temperature. The reaction mixture is filtered through Celite to yield a yellow solution. Concentration under reduced pressure affords an oil, which is purified by chromatography on silica gel to afford 0.62 g of 5-amino-4-methyl-1,3-benzodioxole.

5-Isothiocyanato-4-methyl-1,3-benzodioxole. To a stirred solution of 0.62 g of 5-amino-4-methyl-1,3-benzodioxole in 100 mL of dichloromethane at 25° C. is added 0.94 g of di-2-pyridylthionocarbonate (DPT). The mixture is stirred for six hours. The mixture is concentrated under reduced pressure to give a brown solid mixture, which is purified by chromatography on silica gel to afford 0.78 g of 5-isothiocyanato-4-methyl-1,3-benzodioxole as a white solid.

5-[N'-(2-Aminoethyl)thioureido]-4-methyl-1,3-benzodioxole. To a stirred solution of 0.78 g of 5-isothiocyanato-4-methyl-1,3-benzodioxole in 50 mL of toluene at 25° C. is added 0.80 mL of ethylenediamine. After five minutes, the mixture is concentrated under reduced pressure to yield 1.0 g of 5-[N'-(2-aminoethyl)thioureido]-4-methyl-1,3-benzodioxole as a white solid.

5-(2-Imidazolinylamino)-4-methyl-1,3-benzodioxole, acetic acid salt. To a stirred solution of 1.0 g of 5-[N'-(2-aminoethyl)thioureido]-4-methyl-1,3-benzodioxole in 100 mL of ethanol at 25° C. is added 1.32 g of mercury(II) acetate. After four hours of stirring, the reaction mixture is filtered through Celite and concentrated under reduced pressure to yield a viscous oil, which is purified by chromatography on silica gel to afford 0.95 g of the acetic acid salt of 5-(2-imidazolinylamino)-4-methyl-1,3-benzodioxole.

Example 3

5,8-Dimethyl-1,4-benzodioxane. To a stirred solution of 3.00 g of 3,6-dimethylcatechol and 6.15 g of potassium carbonate in 35 mL of ethylene glycol is added 3.74 mL of dibromoethane. A reflux condenser is attached and the mixture heated in an oil bath to 120° C. for 4 hours. The mixture is allowed to cool to room temperature and then is distributed between 100 mL of saturated potassium carbonate solution and 200 mL of ether. The ether layer is dried over magnesium sulfate and concentrated under reduced pressure to yield a red liquid, which is purified by chromatography on silica gel to afford 2.90 g of 5,8-dimethyl-1,3-benzodioxane as a light yellow liquid.

6-Nitro-5,8-dimethyl-1,4-benzodioxane. A solution of 1.12 mL of concentrated nitric acid in 20 mL of acetic arthydride is added dropwise to a stirred solution of 2.90 g of 5,8-dimethyl-1,3-benzodioxane in 70 mL of acetic anhydride at −5° C. After 15 minutes, the mixture is poured over 100 g of crushed ice and allowed to stir for 30 minutes as a white precipitate falls out of solution. The solid is filtered and taken up in ether, dried over magnesium sulfate and concentrated under reduced pressure to afford 3.1 g of 6-nitro-5,8-dimethyl-1,4-benzodioxane.

6-Amino-5,8-dimethyl-1,4-benzodioxane. A mixture of 3.10 g of 6-nitro-5,8-dimethyl-1,4-benzodioxane and 0.30 g of 10% palladium on carbon in 75 mL of ethanol is placed under a 50 psi hydrogen atmosphere. The mixture is shaken for three hours at room temperature. The reaction mixture is filtered through Celite to yield a brownish solution. Concentration under reduced pressure affords 2.6 g of 6-amino-5,8-dimethyl-1,4-benzodioxane.

6-Isothiocyanato-5,8-dimethyl-1,4-benzodioxane. To a stirred solution of 2.6 g of 6-amino-5,8-dimethyl-1,4-benzodioxane in 100 mL of dichloromethane at 25° C. is added 3.45 g of di-2-pyridylthionocarbonate (DPT). The mixture is stirred for three hours. The mixture is concentrated under reduced pressure to give a brown material, which is purified by chromatography on silica gel to afford 2.9 g of 6-isothiocyanato-5,8-dimethyl-1,4-benzodioxane.

6-[N'-(2-Aminoethyl)thioureido]-5,8-dimethyl-1,4-benzodioxane. A solution of 2.0 g of 6-isothiocyanato-5,8-dimethyl-1,4-benzodioxane in 40 mL of toluene at 25° C. is added to a solution of 2.42 mL of ethylenediamine in 75 mL of toluene. After five minutes, the mixture is concentrated under reduced pressure to 20 mL at which point a solid precipitates from solution. This solid is collected and dried under vacuum to give 2.6 g of 6-[N'-(2-aminoethyl) thioureido]-5,8-dimethyl-1,4-benzodioxane as a white solid.

6-(2-Imidazolinylamino)-5,8-dimethyl-1,4-benzodioxane. To a stirred solution of 2.85 g of 6-[N'-(2-aminoethyl)thioureido]-5,8-dimethyl-1,4-benzodioxane in 100 mL of ethanol at 25° C. is added 2.83 g of mercury(II) acetate. After four hours of stirring, the reaction mixture is filtered through Celite and concentrated under reduced pressure to yield a viscous oil. This material is partitioned into 20 mL of water and 20 mL of chloroform. The aqueous solution is separated and made strongly basic with 1M sodium hydroxide. This solution is extracted with dichloromethane. The organic solution is then dried over magnesium sulfate and concentrated under reduced pressure to afford 1.80 g of 6-(2-imidazolinylamino)-5,8-dimethyl-1,4-benzodioxane as a glassy solid.

Example 4

4,7-Dimethyl-1,3-benzodioxole. To a stirred solution of 2.97 g of 3,6-dimethylcatechol and 3.86 g of potassium carbonate in 60 mL of N,N-dimethylformamide is added 1.69 mL of bromochloromethane. A reflux condenser is attached and the mixture heated in an oil bath to 100° C. for 24 hours. The mixture is allowed to cool to room temperature and then is distributed between 100 mL of water and 200 mL of ether. The aqueous layer is separated and extracted with ether. The combined ether layers are dried over magnesium sulfate and concentrated under reduced pressure to yield a red liquid, which is purified by chromatography on silica gel to afford 2.0 g of 4,7-dimethyl-1,3-benzodioxole as a light yellow liquid.

5-Nitro-4,7-dimethyl-1,3-benzodioxole. A solution of 0.92 mL of concentrated nitric acid in 17 mL of acetic arthydride is added dropwise to a stirred solution of 2.20 g of 4,7-dimethyl-1,3-benzodioxole in 60 mL of acetic anhydride at −5° C. After 30 minutes, the mixture is poured over 100 g of crushed ice and allowed to stir for 30 minutes as a white precipitate falls out of solution. The solid is filtered, taken up in ether, dried over magnesium sulfate and concentrated under reduced pressure to afford 2.1 g of 5-nitro-4,7-dimethyl-1,3-benzodioxole.

5-Amino-4,7-dimethyl-1,3-benzodioxole. A mixture of 1.88 g of 5-nitro-4,7-dimethyl-1,3-benzodioxole and 0.19 g of 10% palladium on carbon in 200 mL of ethanol is placed under a 50 psi hydrogen atmosphere. The mixture is shaken for 90 minutes at room temperature. The reaction mixture is filtered through Celite to yield a brownish solution. Concentration under reduced pressure affords 1.59 g of 5-amino-4,7-dimethyl-1,3-benzodioxole.

5-Isothiocyanato-4,7-dimethyl-1,3-benzodioxole. To a stirred solution of 1.59 g of 5-amino-4,7-dimethyl-1,3-benzodioxole in 60 mL of dichloromethane at 25° C. is added 2.23 g of di-2-pyridylthionocarbonate. The mixture is stirred for 30 minutes. The mixture is concentrated under reduced pressure to give the crude product, which is purified by chromatography on silica gel to afford 1.6 g of 5-isothiocyanato-4,7-dimethyl-1,3-benzodioxole.

5-[N'-(2-Aminoethyl)thioureido]-4,7-dimethyl-1,3-benzodioxole. A solution of 1.6 g of 5-isothiocyanato-4,7-dimethyl-1,3-benzodioxole in 35 mL of toluene at 25° C. is added to a solution of 1.89 g of ethylenediamine in 65 mL of toluene. The reaction gradually turns cloudy as a solid precipitates from solution. This solid is collected and dried under vacuum to give 2.0 g of 5-[N'-(2-aminoethyl) thioureido]-4,7-dimethyl-1,3-benzodioxole as a white solid.

5-(2-Imidazolinylamino)-4,7-dimethyl-1,3-benzodioxole, fumaric acid salt. To a stirred solution of 2.0 g of 5-[N'-(2-aminoethyl)thioureido]-4,7-dimethyl-1,3-benzodioxole in 100 mL of ethanol at 25° C. is added 2.48 g of mercury(II) acetate. After four hours of stirring, the reaction mixture is filtered through Celite and concentrated under reduced pressure to yield a viscous oil, which is purified by chromatography on silica gel to afford the acetic acid salt. This is converted to the fumaric acid salt by dissolving in 10 mL of methanol, followed by addition of 0.88 g of fumaric acid. This solution is diluted with ether until crystallization occurs. The crystals are collected to give 1.19 g of 5-(2-imidazolinylamino)-4,7-dimethyl-1,3-benzodioxole fumarate as a white solid.

Example 5

1-(2-Cyanoethoxy)-2,5-dimethylbenzene. A mixture of 15.0 g of 2,5-dimethylphenol, 16.17 mL of acrylonitrile, and 0.75 mL of Triton-B (a 40% solution of benzyltrimethylammonium hydroxide in methanol) is heated to reflux overnight. The mixture is diluted with ethyl acetate and washed four times with 5% aqueous sodium hydroxide solution, two times with 3N hydrochloric solution, and two times with water. Drying of the organic layer with sodium sulfate, followed by filtration and evaporation provides 17.4 g of 1-(2-cyanoethoxy)-2,5-dimethylbenzene as a brown oil.

1-(2-Carboxyethoxyl-2,5-dimethylbenzene. A mixture of 17.3 g of 1-(2-cyanoethoxy)-2,5-dimethylbenzene, 35 mL of concentrated hydrochloric acid, and 29 mL of formic acid is heated to reflux for six hours. After slight cooling, the mixture is poured into ice water, resulting in formation of a solid. Filtration provides 18.8 g of 1-(2-carboxyethoxy)-2,5-dimethylbenzene.

5,8-Dimethyl-1-dihydrobenzopyran-4-one. A mixture of 9.0 g of 1-(2-carboxyethoxy)-2,5-dimethylbenzene and 91 g of polyphosphoric acid is heated to 100° C. for 20 minutes with occasional stirring. The reaction mixture is poured into 375 mL of ice water, stirred, and extracted four times with methylene chloride. The combined organic layers are dried over sodium sulfate and evaporated to a residue which is purified by chromatography on silica gel to afford 4.22 g of 5,8-dimethyl-1-dihydrobenzopyran-4-one.

5,8-Dimethyl-6-nitro-1-dihydrobenzopyran-4-one. A mixture of 2.0 g of 5,8-dimethyl-1-benzopyran-4-one and 9.4 mL of concentrated sulfuric acid is cooled to 0°–10° C. in an ice bath. To this reaction mixture is added dropwise, over ten minutes, a solution of 1.48 g of concentrated nitric acid and 4.8 mL of concentrated sulfuric acid. The reaction is subsequently stirred for 15 minutes at 0°–10° C. and then at room temperature for 15 minutes. The mixture is poured into ice water and extracted three times with chloroform. The combined organic layers are dried over sodium sulfate and evaporated to provide crude product, which is purified by silica gel chromatography to afford 1.37 of 5, 8-dimethyl-6-nitro-1-dihydrobenzopyran-4-one.

5,8-Dimethyl-6-nitro-1-dihydrobenzopyran. To a solution of 0.711 g of 5,8-dimethyl-6-nitro-1-dihydrobenzopyran-4-one in 5 mL of trifluoroacetic acid is added dropwise 1.8 mL of triethylsilane, and the reaction mixture is stirred at room temperature for 3 days. The mixture is poured into ice water and extracted three times with methylene chloride. The combined organic layers are dried over sodium sulfate and evaporated to provide a crude product, which is purified by silica gel chromatography to afford 0.652 g of 5,8-dimethyl-6-nitro-1-dihydrobenzopyran.

6-Amino-5,8-dimethyl-1-dihydrobenzopyran. A mixture of 0.625 g of 5,8-dimethyl-6-nitro-1-dihydrobenzopyran, 3.4 g of tin(II) chloride dihydrate and 50 mL of ethanol is heated under nitrogen to 60° C. for 3 hours. The cooled reaction mixture is made basic by the addition of aqueous sodium hydroxide solution and extracted three times with methylene chloride. The combined organic layers are dried over sodium sulfate and evaporated to a residue, which is purified by silica gel chromatography to afford 0.287 g of 6-amino-5,8-dimethyl-1-dihydrobenzopyran.

5,8-Dimethyl-6-isothiocyanato-1-dihydrobenzopyran. A mixture of 0.223 g of 6-amino-5,8-dimethyl-1-dihydrobenzopyran, 0.313 g of di-2-pyridylthionocarbonate (DPT), and 0.033 g of dimethylaminopyridine in 13 mL of methylene chloride is stirred at room temperature for 4 hours. The reaction mixture is evaporated to dryness, and the crude product is purified by silica gel chromatography to afford 0.242 g of 5,8-dimethyl-6-isothiocyanato-1-dihydrobenzopyran.

6-[N'-(2-Aminoethyl)thioureido]-5,8-dimethyl-1-dihydrobenzopyran. A solution of 0.215 g of 5,8-dimethyl-6-isothiocyanato-1-dihydrobenzopyran in 5 mL of toluene is added dropwise to a solution of 0.295 g of ethylenediamine in 4 mL of toluene. An additional 5 mL of toluene is used to rinse all of the 5,8-dimethyl-6-isothiocyanato-1-dihydrobenzopyran into the reaction vessel. The mixture is stirred at room temperature for 30 minutes and stored in a freezer for 48 hours. The resulting white solid is filtered, washed with toluene, and dried to give 0.220 g of 6-[N'-(2-aminoethyl)thioureido]-5,8-dimethyl-1-dihydrobenzopyran.

6-(2-Imidazotinylamino)-5,8-dimethyl-1-dihydrobenzopyran. A mixture of 0.201 g of 6-[N'-(2-aminoethyl)thioureido]-5,8-dimethyl-1-dihydrobenzopyran and 0.271 g of mercuric acetate, in 11 mL of methanol is stirred at room temperature for 20 hours. The black mixture is filtered through layers of sand/silica gel/sand, which is washed well with methanol. The methanol flitrate is evaporated, and the crude product is purified by silica gel chromatography to provide 6-(2-imidazolinyl)-5,8-dimethyl-1-dihydrobenzopyran. This material is dissolved in methanol and converted into the fumarate salt by treatment with 0.083 g of fumaric acid. The white solid which forms is recrystallized from methanol-ether to provide 0.092 g of 6-(2-imidaxolinylamino)-5,8-dimethyl-1-dihydrobenzopyran as the hemifumarate salt.

Example 6

2-Methyl-3-(N-trifluoroacetyl)aminophenol. To a solution of 9.48 g of 2-methyl-3-aminophenol and 12.5 mL of pyridine in 200 mL of dimethylformamide is added dropwise 19.6 mL of trifluoroacetic anhydride. The mixture is stirred at room temperature for 2 hours. The reaction mixture is then slowly poured into a saturated sodium bicarbonate solution and stirred for five minutes. The solution is diluted with 300 mL of water and extracted five times with a 4:1 mixture of ether:methylene chloride. The combined organic layers are washed with water and then brine, dried over sodium sulfate, and evaporated to provide 14.57 g of 2-methyl-3-(N-trifluoroacetyl)aminophenol.

t-Butyl 2-[2-methyl-3-(N-trifluoroacetylphenoxyl] acetate. A mixture of 14.27 g of 2-methyl-3-(N-trifluoroacetyl)aminophenol, 14.6 g of t-butyl bromoacetate, 9.9 g of potassium carbonate and 200 mL of acetone is heated at reflux for 40 hours. The mixture is filtered, and the filtrate is evaporated. The resulting crude product is purified by silica gel chromatography to provide 13.4 g of t-butyl 2-[2-methyl-3-(N-trifluoroacetylphenoxy)]acetate.

7-Methyl-6-(N-trifluoroacetyl)amino-2,3-dihydrobenzofuran-3-one. A mixture of 0.33 g of t-butyl 2-[2-methyl-3-(N-trifluoroacetylphenoxy)] acetate, 4 mL of trifluoroacetic acid, and 4 mL of methylene chloride is stirred at room temperature for one hour and then concentrated by evaporation. The resulting white solid is taken up in 4 mL of methylene chloride, and 0.38 g of oxalyl chloride and 0.009 g of dimethylformamide are added. The mixture is stirred at room temperature for 2.5 hours and concentrated by evaporation. The resulting residue is twice dissolved in dichloroethane, and the mixture evaporated to dryness. The resulting solid acid chloride is dissolved in 9 ml of dichloroethane and added to a suspension of 0.44 g of aluminum chloride in 7 mL of dichloroethane. The reaction mixture is stirred at room temperature for two hours and then poured into an aqueous sodium bicarbonate solution. The mixture is extracted four times with dichloroethane, and the combined organic layers are washed consecutively with sodium bicarbonate solution, water, and brine. Drying over sodium sulfate and evaporation provides a crude product, which is purified by silica gel chromatography to give rise to 0.054 g of 7-methyl-6-(N-trifluoroacetyl)aminodihydrobenzofuran-3-one.

7-Methyl-6-(N-trifluoroacetyl)amino-2,3-dihydrobenzofuran. A mixture of 1.04 g of 7-methyl-6-(N-trifluoroacetyl)aminodihydrobenzofuran-3-one, 6.2 mL of trifluoroacetic acid, and 1.86 g of triethylsilane is heated and stirred at 55°–60° C. for 72 hours. The mixture is evaporated, and the crude product is purified by silica gel chromatography to afford 0.255 g of 7-methyl-6-(N-trifluoroacetyl)amino-2,3-dihydrobenzofuran.

6-Amino-7-methyl-2,3-dihydrobenzofuran. A mixture of 0.245 g of 7-methyl-6-(N-trifluoroacetyl)amino-2,3-dihydrobenzofuran, 1 mL of a 3N potassium hydroxide solution and 5 mL of ethanol is refluxed for one hour. The reaction mixture is poured into 40 mL of water and extracted three times with a 4:1 mixture of ether:methylene chloride. The combined organic layers are washed with water and then brine, dried over sodium sulfate, and evaporated to give 0.149 g of 6-amino-7-methyl-2,3-dihydrobenzofuran.

7-Methyl-6-isothiocyanato-2,3-dihydrobenzofuran. A mixture of 0.149 g of 6-amino-7-methyl-2,3-dihydrobenzofuran, 0.249 g of di-2-pyridylthionocarbonate (DPT), 0.026 g of dimethylaminopyridine and 7 mL of methylene chloride is stirred at room temperature for 2 hours. The reaction mixture is evaporated, and the crude product is purified by silica gel chromatography to provide 0.154 g of 7-methyl-6-isothiocyanato-2,3-dihydrobenzofuran.

6-[N'-(2-aminoethyl)thioureido]-7-methyl-2,3-dihydrobenzofuran. To a solution of 0.205 g of ethylenediamine in 1 mL of methylene chloride is added dropwise a solution of 0.13 g of 7-methyl-6-isothiocyanato-2,3-dihydrobenzofuran in 2 mL of methylene chloride. The mixture is stirred at room temperature for 1 hour and evaporated to provide 6-[N'-(2-aminoethyl)thioureido]-7-methyl-2,3-dihydrobenzofuran as the crude product.

6-(2-Imidazolinylamino-7-methyl-2,3-dihydrobenzofuran hemiacetate. The above crude 6-[N'-(2-aminoethyl)thioureido]-7-methyl-2,3-dihydrobenzofuran is dissolved in 3 mL of methanol and treated with 0.25 g of mercuric acetate, forming a black color. The reaction mixture is stirred overnight at room temperature. The reaction mixture is filtered through celite, concentrated, and purified by silica gel chromatography to provide 0.131 g of 6-(2-imida zolinylamino)-7-methyl-2,3-dihydrobenzofuran as the hemiacerate salt.

Another aspect of the subject invention is compositions which comprise a safe and effective amount of a subject compound, or a pharmaceutically-acceptable salt thereof, and a pharmaceutically-acceptable carrier. As used herein, "safe and effective amount" means an amount of the subject compound sufficient to significantly induce a positive modification in the condition to be treated, but low enough to avoid serious side effects (at a reasonable benefit/risk ratio), within the scope of sound medical judgement. A safe and effective amount of the subject compound will vary with the age and physical condition of the patient being treated, the severity of the condition, the duration of the treatment, the nature of concurrent therapy, the particular pharmaceutically-acceptable carrier utilized, and like factors within the knowledge and expertise of the attending physician.

Compositions of the subject invention preferably comprise from about 0.0001% to about 99.9% by weight of the subject compound, more preferably from about 0.01% to about 10%, more preferably still from about 0.1% to about 5%, and also preferably from about 0.5% to about 1%.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the composition are capable of being comingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; algenic acid; emulsifiers, such as the Tweens®; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

The preferred mode of administering the subject compounds is perorally. The preferred unit dosage form is therefore tablets, capsules, lozenges, chewable tablets, and the like, such unit dosage forms comprise a safe and effective amount of the subject compound, which is preferably from about 0.01 mg to about 200 mg, more preferably from about 0.1 mg to about 50 mg, more preferably still from about 0.5 mg to about 25 mg, also preferably from about 1 mg to about 10 mg. The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Gildants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Such liquid oral compositions preferably comprise from about 0.001% to about 5% of the subject compound, more preferably from about 0.01% to about 0.5%. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel® RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Other compositions useful for attaining systemic delivery of the subject compounds include sublingual and buccal dosage forms. Such compositions typically comprise one or more of soluble filler substances such as sucrose, sorbitol and mannitol; and binders such as acacia, microcrystalline cellulose, carboxymethyl cellulose and hydroxypropylmethyl cellulose. Gildants, lubricants, sweeteners, colorants, antioxidants and flavoring agents disclosed above may also be included.

A preferred mode of administering the subject compounds is topically to the site where activity is desired: intranasal doses for nasal decongestion, inhalants for asthma, eye drops, gels and creams for ocular disorders, and peroral doses for gastrointestinal disorders.

Preferred compositions of the subject invention include aqueous solutions comprising a safe and effective amount of a subject compound intended for topical intranasal administration. Such compositions preferably comprise from about 0.001% to about 5% of a subject compound, more preferably from about 0.01% to about 0.5%. Such compositions also typically include safe and effective amounts of preservatives, such as benzalkonium chloride and thimerosal; buffers such as phosphate and acetate; tonicity agents such as sodium chloride; antioxidants such as ascorbic acid; aromatic agents; and acids and bases to adjust the pH of these aqueous compositions as needed.

Preferred compositions of the subject invention include aqueous solutions, suspensions, and dry powders comprising a safe and effective amount of a subject compound intended for atomization and topical inhalation administration. Such compositions preferably comprise from about 0.1% to about 50% of a subject compound, more preferably from about 1% to about 20%. Such compositions are typically contained in a container with attached atomizing means. Such compositions also typically include propellants such as chlorofluorocarbons 12/11 and 12/114; solvents such as water, glycerol and ethanol; stabilizers such as ascorbic acid, sodium metabisulfite; preservatives such as cetylpyridinium chloride and benzalkonium chloride; tonicity adjustors such as sodium chloride; and flavoring agents such as sodium saccharin.

Preferred compositions of the subject invention include aqueous solutions comprising a safe and effective amount of a subject compound intended for topical intraocular administration. Such compositions preferably comprise from about 0.0001% to about 5% of a subject compound, more preferably from about 0.01% to about 0.5%. Such compositions also typically include one or more of preservatives, such as benzalkonium chloride, thimerosal, phenylmercuric acetate; vehicles, such as poloxamers, modified celluloses, povidone and purified water; tonicity adjustors, such as sodium chloride, mannitol and glycerin; buffers such as acetate, citrate, phosphate and borate; antioxidants such as sodium metabisulfite, butylated hydroxy toluene and acetyl cysteine; acids and bases may be used to adjust the pH of these formulations as needed.

Preferred compositions of the subject invention include solids, such as tablets and capsules, and liquids, such as solutions, suspensions and emulsions (preferably in soft gelatin capsules), comprising a safe and effective amount of a subject compound intended for topical administration to the gastrointestinal tract by peroral administration. Such compositions preferably comprise from about 0.01 mg to about 100 mg per dose, more preferably from about 0.1 mg to about 5 mg per dose. Such compositions can be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropylmethyl cellulose phthalate, ethyl cellulose, waxes and shellac.

Compositions of the subject invention may optionally include other drug actives. Non-limiting examples of drug actives which may be incorporated in the subject compositions, and typical dosage amounts of them, include: respiratory drug actives: classical antihistamines, e.g., chlorpheniramine from about 1 mg to about 4 mg per dose, and diphenhydramine from about 10 mg to about 50 mg per dose; nonsedating antihistamines, e.g., terrenadine from about 30 mg to about 60 mg per dose, loratadine from about 5 mg per dose to about 10 mg per dose, and cetirizine from about 5 mg per dose to about 10 mg per dose; expectorants, e.g., guaifenesin from about 100 mg to about 200 mg per dose; antitussives, e.g., dextromethorphan from about 5 mg to about 30 mg per dose; and analgesics, e.g., ibuprofen from about 100 mg to about 800 mg per dose, and acetaminophen from about 80 mg to about 1000 mg per dose; ocular drug actives: acetylcholinesterase inhibitors, e.g., echothiophate from about 0.03% to about 0.25% in topical solution; and gastrointestinal actives: antidiarrheals, e.g., loperamide from about 0.1 mg to about 1.0 mg per dose, and bismuth subsalicylate from about 25 mg to about 300 mg per dose.

Another aspect of the subject invention involves methods for preventing or treating nasal congestion by administering a safe and effective amount of a subject compound to a human or lower animal experiencing or at risk of experiencing nasal congestion. Each administration of a dose of the subject compound preferably administers a dose within the range of from about 0.001 mg/kg to about 10 mg/kg of a compound, more preferably from about 0.01 mg/kg to about 5 mg/kg, more preferably still from about 0.1 mg/kg to about 1 mg/kg. The frequency of administration of a subject compound according to the subject invention is preferably from about once to about six times daily, more preferably from about 2 times to about 4 times daily. Such doses and frequencies are also preferred for treating other respiratory conditions, such as cough, COPD and asthma.

Another aspect of the subject invention involves methods for preventing or treating glaucoma by administering a safe and effective amount of a subject compound to a human or lower animal experiencing or at risk of experiencing glaucoma. Each administration of a dose of the subject compound preferably administers a dose within the range of from about 0.01 µg/kg to about 10 mg/kg of a compound, more preferably from about 0.001 mg/kg to about 1 mg/kg, more preferably still from about 0.01 mg/kg to about 0.1 mg/kg. The frequency of administration of a subject compound according to the subject invention is preferably from about once to about six times daily, more preferably from about 2 times to about 4 times daily.

Another aspect of the subject invention involves methods for preventing or treating functional bowel disorders, such as diarrhea, by administering a safe and effective amount of a subject compound to a human or lower animal experiencing or at risk of experiencing diarrhea. Each administration of a dose of the subject compound preferably administers a dose within the range of from about 0.001 mg/kg to about 10 mg/kg of a compound, more preferably from about 0.01 mg/kg to about 5 mg/kg, more preferably still from about 0.1 mg/kg to about 1 mg/kg. The frequency of administration of a subject compound according to the subject invention is preferably from about once to about six times daily, more preferably from about 2 times to about 4 times daily.

The following non-limiting examples illustrate the compounds, compositions and methods of use of the subject invention.

Example 7

Oral Tablet Composition

| Ingredient | Amount Per tablet (mg) |
| --- | --- |
| Compound 1 | 20.0 |
| Microcrystalline cellulose (Avicel PH 102 ®) | 80.0 |
| Dicalcium phosphate | 96.0 |
| Pyrogenic silca (Cab-O-Sil ®) | 1.0 |
| Magnesium stearate | 3.0 |
| Total = | 200.0 |

Example 8

Chewable Tablet Composition

| Ingredient | Amount per tablet (mg) |
| --- | --- |
| Compound 2 | 15.0 |
| Mannitol | 255.6 |
| Microcrystalline cellulose (Avicel PH 101 ®) | 100.8 |

-continued

Chewable Tablet Composition

| Ingredient | Amount per tablet (mg) |
|---|---|
| Dextrinized sucrose (Di-Pac ®) | 199.5 |
| Imitation orange flavor | 4.2 |
| Sodium saccharin | 1.2 |
| Stearic acid | 15.0 |
| Magnesium stearate | 3.0 |
| FD&C Yellow #6 dye | 3.0 |
| Pyrogenic silica (Cab-O-Sil ®) | 2.7 |
| Total = | 600.0 |

One tablet is chewed and swallowed by a patient with nasal congestion. The congestion is substantially reduced.

Example 9

Sublingual Tablet Composition

| Ingredient | Amount per tablet (mg) |
|---|---|
| Compound 3 | 2.00 |
| Mannitol | 2.00 |
| Microcrystalline cellulose (Avicel PH 101 ®) | 29.00 |
| Mint flavorants | 0.25 |
| Sodium saccharin | 0.08 |
| Total = | 33.33 |

One tablet is placed under the tongue of a patient with nasal congestion and allowed to dissolve. The congestion is rapidly and substantially diminished.

Example 10

Intranasal Solution Composition

| Ingredient | Composition (% w/v) |
|---|---|
| Compound 1 | 0.20 |
| Benzalkonium chloride | 0.02 |
| Thimerosal | 0.002 |
| d-Sorbitol | 5.00 |
| Glycine | 0.35 |
| Aromatics | 0.075 |
| Purified water | q.s. |
| Total = | 100.00 |

One-tenth of a mL of the composition is sprayed from a pump actuator into each nostril of a patient with nasal congestion. The congestion is substantially diminished.

Example 11

Intranasal Gel Composition

| Ingredient | Composition (% w/v) |
|---|---|
| Compound 4 | 0.10 |
| Benzalkonium chloride | 0.02 |
| Thimerosal | 0.002 |
| Hydroxypropyl methylcellulose (Metolose 65SH4000 ®) | 1.00 |

-continued

Intranasal Gel Composition

| Ingredient | Composition (% w/v) |
|---|---|
| Aromatics | 0.06 |
| Sodium chloride (0.65%) | q.s. |
| Total = | 100.00 |

One-fifth of a mL of the composition is applied as drops from a dropper into each nostril of a patient with nasal congestion. The congestion is substantially reduced.

Example 12

Inhalation Aerosol Composition

| Ingredient | Composition (% w/v) |
|---|---|
| Compound 5 | 5.0 |
| Alcohol | 33.0 |
| Ascorbic acid | 0.1 |
| Menthol | 0.1 |
| Sodium Saccharin | 0.2 |
| Propellant (F12, F114) | q.s. |
| Total = | 100.0 |

Two-puffs of the aerosol composition is inhaled from a metered-dose inhaler by a patient with asthma. The asthmatic condition is effectively relieved.

Example 13

Topical Opthalmic Composition

| Ingredient | Composition (% w/v) |
|---|---|
| Compound 6 | 0.10 |
| Benzalkonium chloride | 0.01 |
| EDTA | 0.05 |
| Hydroxyethylcellulose (Natrosol M ®) | 0.50 |
| Sodium metabisulfite | 0.10 |
| Sodium chloride (0.9%) | q.s. |
| Total = | 100.0 |

One-tenth of a mL of the composition is administered directly into each eye of a patient with glaucoma. The intraocular pressure is substantially reduced.

Example 14

Oral Liquid Composition

| Ingredient | Amount/15 mL Dose |
|---|---|
| Compound 5 | 15 mg |
| Chlorpheniramine maleate | 4 mg |
| Propylene glycol | 1.8 g |
| Ethanol (95%) | 1.5 mL |
| Methanol | 12.5 mg |
| Eucalyptus oil | 7.55 mg |
| Flavorants | 0.05 mL |
| Sucrose | 7.65 g |
| Carboxymethylcellulose (CMC) | 7.5 mg |
| Microcrystalline cellulose and Sodium CMC (Avicel RC 591 ®) | 187.5 mg |
| Polysorbate 80 | 3.0 mg |
| Glycerin | 300 mg |

-continued

| Oral Liquid Composition | |
|---|---|
| Ingredient | Amount/15 mL Dose |
| Sorbitol | 300 mg |
| FD&C Red #40 dye | 3 mg |
| Sodium saccharin | 22.5 mg |
| Sodium phosphate monobasic | 44 mg |
| Sodium citrate monohydrate | 28 mg |
| Purified Water | q.s. |
| Total = | 15 mL |

One 15 mL dose of the liquid composition is swallowed by a patient with nasal congestion and runny nose due to allergic rhinitis. The congestion and runny nose are effectively reduced.

Example 15

| Oral Liquid Composition | |
|---|---|
| Ingredient | Amount/15 mL Dose |
| Compound 4 | 30 mg |
| Sucrose | 8.16 g |
| Glycerin | 300 mg |
| Sorbitol | 300 mg |
| Methylparaben | 19.5 mg |
| Propylparaben | 4.5 mg |
| Menthol | 22.5 mg |
| Eucalyptus oil | 7.5 mg |
| Flavorants | 0.07 mL |
| FD&C Red #40 dye | 3.0 mg |
| Sodium saccharin | 30 mg |
| Purified water | q.s. |
| Total = | 15 mL |

One 15 mL dose of the alcohol-free liquid medication is swallowed by a patient with nasal congestion. The congestion is substantially diminished.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A compound having the following structure:

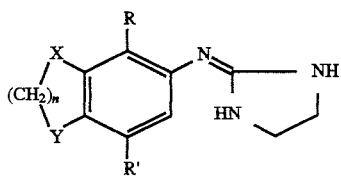

wherein (a) n is an integer from 1 to about 3;

(b) X and Y are each independently selected from O, S and $CH_2$, with at least one of X and Y being O or S;

(c) R is unsubstituted, straight or branched chain alkanyl or alkanoxy having from 1 to about 3 non-hydrogen atoms; and (d) R' is selected from the group consisting of hydrogen, methyl, cyano, and halo.

2. The compound of claim 1 wherein R is methyl or ethyl, and R' is hydrogen or methyl.

3. The compound of claim 2 wherein R' is hydrogen.

4. The compound of claim 1 wherein n is 1 or 2, and both X and Y are independently either O or S.

5. The compound of claim 4 wherein R is methyl, ethyl or methoxy atoms.

6. The compound of claim 4 wherein X and Y are both O, and R is methyl or ethyl.

7. The compound of claim 6, wherein R is methyl.

8. The compound of claim 6 wherein R is methyl, R' is hydrogen or methyl, and n is 1.

9. The compound of claim 6 wherein R is methyl, R' is hydrogen or methyl, and n is 2.

10. The compound of claim 1 wherein n is 1 or 2, X is O or S, and Y is $CH_2$.

11. The compound of claim 10 wherein R is methyl, ethyl or methoxy.

12. The compound of claim 10 wherein X is O, and R is methyl or ethyl.

13. The compound of claim 12 wherein n is 1, R is methyl and R' is hydrogen.

14. The compound of claim 1 wherein n is 1 or 2, X is $CH_2$, and Y is O or S.

15. The compound of claim 14 wherein R is methyl, ethyl or methoxy and R' is methyl, halo or cyano.

16. The compound of claim 15 wherein Y is O, and R is methyl or ethyl.

17. The compound of claim 16 wherein n is 2 and both R and R' are methyl.

18. A pharmaceutical composition comprising:

(a) a safe and effective amount of a compound of any of claims 1, 8, 9, 13, and 17; and (b) a pharmaceutically-acceptable carrier.

19. A method for treating nasal congestion by administering to a human or lower animal in need of such treatment a safe and effective amount of a compound of any one of claims 1, 8, 9, 13, and 17.

20. A compound of claim 1 wherein X and Y are S.

21. A compound of claim 1 wherein X is S and Y is O.

22. A compound of claim 1 wherein X is O and Y is S.

* * * * *